(12) United States Patent
Carter

(10) Patent No.: US 7,253,147 B2
(45) Date of Patent: *Aug. 7, 2007

(54) MODIFIED SERUM ALBUMIN WITH REDUCED AFFINITY FOR NICKEL AND COPPER

(75) Inventor: Daniel C. Carter, Madison, AL (US)

(73) Assignee: New Century Pharmaceuticals, Inc., Huntsville, AL (US)

(*) Notice: Subject to any disclaimer, the term of this patent is extended or adjusted under 35 U.S.C. 154(b) by 207 days.

This patent is subject to a terminal disclaimer.

(21) Appl. No.: 10/934,401

(22) Filed: Sep. 7, 2004

(65) Prior Publication Data

US 2005/0020815 A1 Jan. 27, 2005

Related U.S. Application Data

(62) Division of application No. 09/616,962, filed on Jul. 14, 2000, now Pat. No. 6,787,636.

(51) Int. Cl.
*A61K 38/38* (2006.01)
*C07K 14/765* (2006.01)

(52) U.S. Cl. ........................ 514/12; 530/363

(58) Field of Classification Search ............ None
See application file for complete search history.

(56) References Cited

U.S. PATENT DOCUMENTS

| | | | | |
|---|---|---|---|---|
| 6,475,743 | B1 * | 11/2002 | Bar-Or et al. | 435/7.1 |
| 2003/0180820 | A1 * | 9/2003 | Bar-Or et al. | 435/7.32 |

FOREIGN PATENT DOCUMENTS

| | | |
|---|---|---|
| EP | 0 180 968 | 5/1986 |
| EP | 0 244 859 | 11/1987 |
| WO | WO 00/20454 | 4/2000 |
| WO | WO 01/91713 A1 | 6/2001 |
| WO | WO 02/05645 A1 | 1/2002 |
| WO | WO 02/49671 | 6/2002 |

OTHER PUBLICATIONS

D.C. Carter et al., "Structure of Serum Albumin," Advances in Protein Chemistry, 1994, vol. 45, pp. 153-203.*
Takhashi et al., "Structural changes and metal binding by proalbumins and other amino-terminal . . . ", Proceedings of the National Academyy of Sciences, vol. 84, Nov. 1987, pp. 7403-7407.
Bar-Or et al., "Characterization of the CO2+ and NI2+ Binding Amino-Acid Residues . . . ", European Journal of Biochemistry, vol. 268, No. 1, Jan. 2001, pp. 42-47.
Database WPI, Derwent Publications, SHAN—1995-200996, Apr. 20, 1994.
Chan et al., "Site-specific N-terminal auto-degradation of human serum albumin", European Journal of Biochemistry, vol. 227, No. 1-2, 1995, pp. 524-528.
Sadler et al., Involvement of a lysine residue in the N-terminal Ni2+ and Cu2+ binding site of serum albumins, European Journal of Biochemistry, vol. 220, No. 1, 1994, pp. 193-200.

* cited by examiner

*Primary Examiner*—Robert A. Wax
(74) *Attorney, Agent, or Firm*—B. Aaron Schulman; Stites & Harbison PLLC

(57) ABSTRACT

A modified serum albumin is provided which has been modified in the n-terminal region or binding region VI, such as through a truncation of at least three amino acids at the n-terminal end, so that it exhibits reduced or eliminated binding of trace metals such as nickel and/or copper. Other suitable modifications to this binding region include mutations such as an elongation or insertion which will be sufficient to disrupt the trace metal binding which is highest at this site. The modified albumin of the present invention is advantageous in that its binding to trace metals is reduced or eliminated, and it can thus be used more safely and effectively than unmodified albumin with a reduced or eliminated likelihood of causing an allergic reaction to the trace metal in the human being treated with the albumin composition.

6 Claims, 2 Drawing Sheets

```
                       SEQUENCE LISTING

<160> NUMBER OF SEQ ID NOS: 5

<210> SEQ ID NO 1
<211> LENGTH: 5
<212> TYPE: PRT
<213> ORGANISM: Homo sapiens

<400> SEQUENCE: 1

Ala His Lys Ser Glu
1               5

<210> SEQ ID NO 2
<211> LENGTH: 4
<212> TYPE: PRT
<213> ORGANISM: Homo sapiens

<400> SEQUENCE: 2

His Lys Ser Glu
1

<210> SEQ ID NO 3
<211> LENGTH: 6
<212> TYPE: PRT
<213> ORGANISM: Homo sapiens

<400> SEQUENCE: 3

Asp Ala His Lys Ser Glu
1               5

<210> SEQ ID NO 4
<211> LENGTH: 6
<212> TYPE: PRT
<213> ORGANISM: Homo sapiens
<220> FEATURE:
```

```
<221> NAME/KEY: MISC_FEATURE
<222> LOCATION: (3)..(3)
<223> OTHER INFORMATION: X can be any amino acid.

<400> SEQUENCE: 4

Asp Ala Xaa Lys Ser Glu
1               5

<210> SEQ ID NO 5
<211> LENGTH: 7
<212> TYPE: PRT
<213> ORGANISM: Homo sapiens

<400> SEQUENCE: 5

Glu Ala Glu Phe Asp Ala His
1               5
```

MODIFIED SERUM ALBUMIN WITH REDUCED AFFINITY FOR NICKEL AND COPPER

CROSS-REFERENCE TO RELATED APPLICATIONS

This application is a divisional of application Ser. No. 09/616,962, filed Jul. 14, 2000 now U.S. Pat. No. 6,787,636.

FIELD OF THE INVENTION

This invention relates in general to a modified serum albumin useful as a blood volume expander, and in particular to a recombinant or otherwise modified serum albumin that is mutated such as by truncation, elongation or insertion at its n-terminal region which has improvements in its metal binding properties and reduced affinity for metal elements such as nickel or copper and which can thus be used safely and effectively in a variety of applications including use as a blood volume expander, for excipient and culture media applications, or as additives or substitutes in a wide range of products including medicines, cosmetics, dairy products and dietary supplements which would normally utilize unmodified forms of albumin or related compounds.

BACKGROUND OF THE INVENTION

The serum albumins belong to a multigene family of proteins that includes alpha-fetoprotein and human group-specific component, also known as vitamin-D binding protein. The members of this multigene family are typically comprised of relatively large multi-domain proteins, and the serum albumins are the major soluble proteins of the circulatory system and contribute to many vital physiological processes. Serum albumin generally comprises about 50% of the total blood component by dry weight, and as such is responsible for roughly 80% of the maintenance of colloid osmotic blood pressure and is chiefly responsible for controlling the physiological pH of blood.

The albumins and their related blood proteins also play an extremely important role in the transport, distribution and metabolism of many endogenous and exogenous ligands in the human body, including a variety of chemically diverse molecules including fatty acids, amino acids, steroids, calcium, metals such as copper and zinc, and various pharmaceutical agents. The albumin family of molecules are generally thought to facilitate transfer many of these ligands across organ-circulatory interfaces such as the liver, intestines, kidneys and the brain, and studies have suggested the existence of an albumin cell surface receptor. See, e.g., Schnitzer et al., *P.N.A.S.* 85:6773 (1988). The albumins are thus intimately involved in a wide range of circulatory and metabolic functions.

Human serum albumin (HSA) is a protein of about 66,500 kD and is comprised of 585 amino acids including at least 17 disulphide bridges. As with many of the members of the albumin family, human serum albumin plays an extremely important role in human physiology and is located in virtually every human tissue and bodily secretion. As indicated above, HSA has an outstanding ability to bind and transport a wide spectrum of ligands throughout the circulatory system including the long-chain fatty acids which are otherwise insoluble in circulating plasma. The atomic structure and particular details regarding the binding affinities of albumin and the specific regions primarily responsible for those binding properties have been previously determined as set forth, e.g., in U.S. patent application Ser. No. 08/448,196, filed May 25, 1993, now U.S. Pat. No. 5,780,594 and U.S. patent application Ser. No. 08/984,176, filed Dec. 3, 1997, now U.S. Pat. No. 5,948,609, both of which are incorporated herein by reference.

In addition to human serum albumin, studies have been made on albumins in a variety of animal species, and it has been determined that over 60% of the amino acid sequences are conserved among the known albumin sequences of many mammals such as bovine, rat and human serum albumin. Moreover, as more and more albumins from other animal species have been sequenced, it has been found that the albumins from a wide range of vertebrate species including sheep, frogs, salmon, mice, pigs and even sea lampreys share varying degrees of sequence homology, and all share the characteristic repeating pattern of disulphide bridges observed in human serum albumin, thus implying a common three-dimensional structure. Furthermore, all members of the albumin multigene family for which sequences have been determined appear to have internal sequence homology (from two- to seven-fold), thus suggesting that the proteins evolved from a common ancestral protein, and reflecting the vital nature and function of this protein. See, e.g., Carter et al., *Science* 244:1195 (1989).

Because of the vital role played by albumins, there are literally thousands of applications for serum albumin and its related proteins covering a wide range of physiological conditions, and most often, native serum albumin has been used. However, unlike blood proteins such as hemoglobin, native serum albumins are non-functional as oxygen transport systems, and thus have not been useful in blood replacement systems requiring oxygen transport. More recently, an oxygen-transporting albumin-based blood replacement composition was developed which can be utilized as a blood volume expander, as has been disclosed in U.S. Pat. No. 5,948,609, incorporated herein by reference, and this composition further increases the importance and usefulness of serum albumin.

Additionally, in applications involving albumin, it has been known to utilize the human serum albumin sequence of the prototypical or major allotype of the human serum albumin sequence, which has included the well known n-terminal amino acid sequence n-DAHK-c. See, e.g., Carter et al., Advances in Protein Chemistry, Vol. 45, 153–203 (1994) and Peters, "All About Albumin", Academic Press (1995). The binding of copper and nickel to the n-terminal peptide of albumins has been known and studied for many years, and this site has been designated as functional binding location Site VI in Carter et al. (1994). The sequence X—X-Histidine appears to be the key to the copper and nickel metal binding at this site, and of additional importance is the structural flexibility of the n-terminal polypeptide which cannot be structurally hindered.

At physiological pH, copper is bound with extraordinarily high affinity to this site ($K_a=1.6 \times 10^{16}$ $M^{-1}$) (see Camerman et al., *Can. J. Chem.*, Vol. 54:1309–1316 (1976)), perhaps the highest reported binding constant of any bound ligand to serum albumin. By comparison, the binding for Nickel is $K_a = 3 \times 10^5$ $M^{-1}$. See Lau et al., *J. Biol. Chem.* Vol. 249: 5878–5884 (1974). While this feature of the albumin molecule serves to protect the body from the potential damaging influences of the metals, especially copper, the nickel complex with albumin is known to elicit allergic reactions in some individuals, which occurs following ingestion of Ni(II) or exposure to nickel plated jewelry or other similar items. For example, an occupational asthma resulting from nickel binding is well recognized and has been traced to antibodies against Ni(II) specifically bound to the n-terminus of human serum albumin. See Carter et al. (1994), supra and Nieboer et al., *Br. J. Ind. Med.*, Vol. 41:56–63 (1984).

In the normal course of recombinant production of albumin and other proteins, there is usually a given level of certain metals, including nickel and copper, which are required as components of the culture media and used in albumin production. Consequently, a significant level of nickel, copper and/or other metals is chelated by the n-terminal peptide of albumin during production, as evidenced during production by the green and yellow coloration of the recombinant human serum albumin. However, the presence of these metals, even in trace amounts, in the albumin produced via recombinant methods can lead to significant health problems as indicated above.

There is thus a significant need to develop safe and effective serum albumin products for use in many applications, particularly those which involve use in humans either internally or externally, which can reduce or eliminate the high affinity of albumin to copper and nickel and/or other metals, and which can thus reduce the risk that a potential albumin-based product will elicit an allergic response to the bound metal in a human or animal who is being treated with an albumin composition.

SUMMARY OF THE INVENTION

Accordingly, it is thus an object of the present invention to provide a novel serum albumin composition in which the affinity to trace metals such as nickel and/or copper is reduced or eliminated.

It is further an object of the present invention to provide a novel modified serum albumin having reduced affinity to trace metals which can be utilized in a variety of applications including as a blood replacement product, a cosmetic, a medicament, or a pharmaceutical additive.

It is still further an object of the present invention to provide a novel serum albumin product which has improved clarity so as to become more useful in scientific applications involving spectroscopy.

It is even further an object of the present invention to provide a novel serum albumin-based blood replacement product which not only encompasses a variety of useful physiological functions including oxygen transport and expansion of blood volume, but which can be utilized safely in humans and animals and which has reduced or eliminated binding to trace metals such as nickel and/or copper and thus presents a greatly reduced risk of causing an allergic reaction or other harmful conditions.

These and other objects are achieved by virtue of the present invention which provides a modified serum albumin which has been either truncated by at least one amino acid at its n-terminal end or which has been mutated in such a way as to disrupt the metal binding site of the serum albumin previously identified as binding site VI. These changes and mutations to this binding site include elongation, insertion or other changes to the n-terminal end, such as to the histidine at amino acid position 3, which are sufficient so as to either sterically hinder the binding site VI or eliminate vital binding interactions, and thus reduce the affinity of this region to metals such as nickel and/or copper. As a result of these modifications, which may be made either recombinantly or through other suitable physical or chemical means, the resulting serum albumin composition will have greatly reduced or totally eliminated binding to the trace metals, and can thus be used safely and effectively in a variety of applications, including as a blood product, a cosmetic, a medicament, a pharmaceutical additive, or numerous other applications which presently employ albumin compositions.

These and other features of the present invention are set forth in, or will become obvious from, the detailed description of the preferred embodiments provided hereinbelow.

BRIEF DESCRIPTION OF THE DRAWING FIGURES

The present invention will now be described in detail with respect to preferred embodiments thereof, which are to be taken together with the accompanying drawings, wherein.

DETAILED DESCRIPTION OF THE PREFERRED EMBODIMENTS

Figure 1:
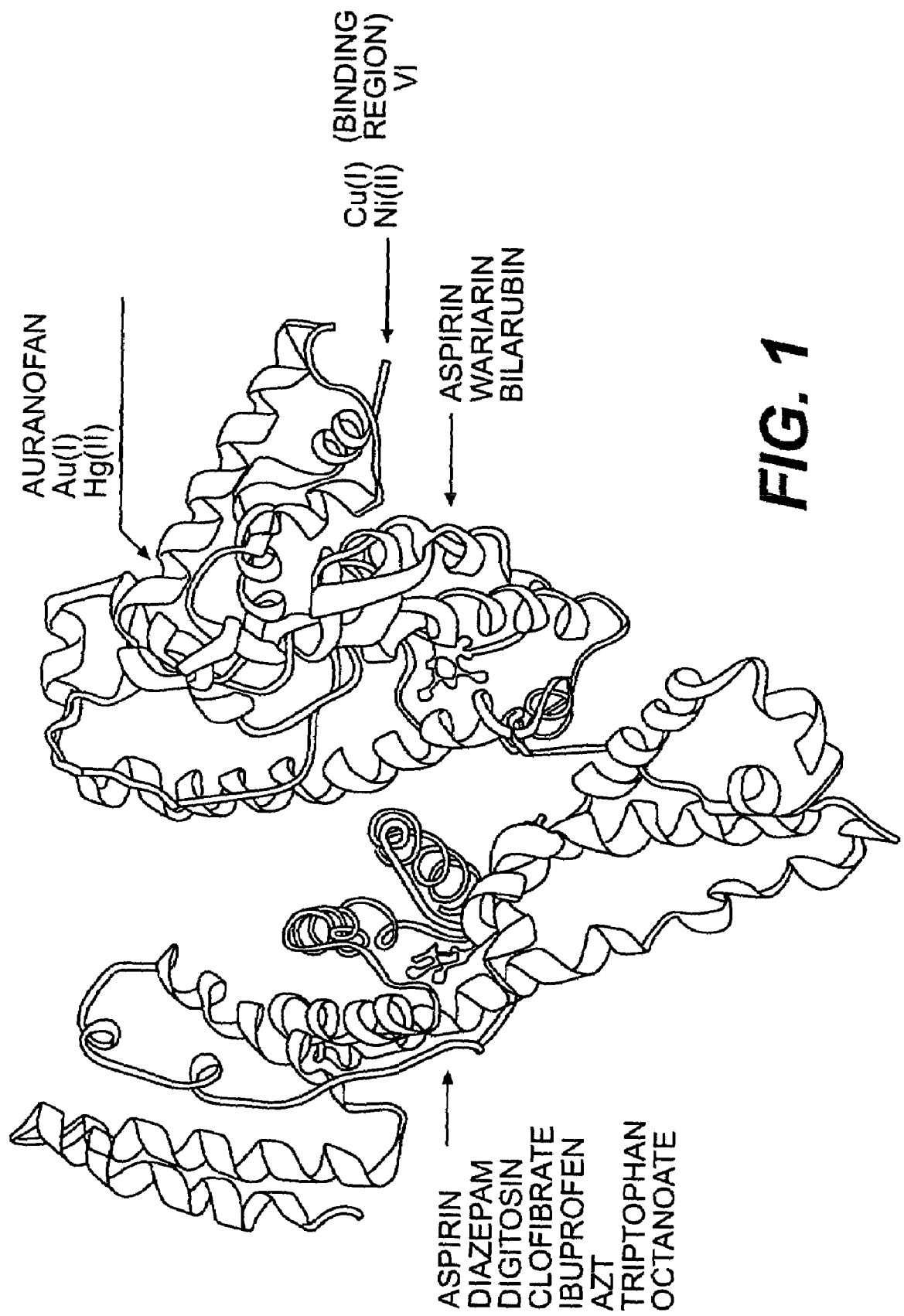
FIG. 1 is a view of the structure of human serum albumin illustrating the binding region VI as determined crystallographically.

In accordance with the present invention, a modified human serum albumin is provided which is modified at the binding site VI, or the n-terminal region, so as to have reduced or eliminated affinity to trace metals such as nickel and/or copper. A schematic crystallographic view of a human serum albumin crystal showing some of the albumin binding regions including binding region VI is shown in FIG. 1. By human serum albumin, it will be understood that this refers to the human form of the serum albumin protein, or any other serum albumin protein that operates in a similar manner to the human serum albumin and has binding sites with similar properties. Accordingly, any serum albumin that has sufficient similarity with regard to the properties of binding region VI, e.g., other serum albumins including bovine serum albumin (BSA), are contemplated as useful in accordance with the invention. In addition, it will also be the case that other peptides, fragments, or other subunits that contain the binding region VI of human serum albumin or which are equivalent to this region and have the same properties will also fall within the scope of the invention since these fragments or subunits may be isolated and perform in the same manner as an natural albumin which contains this binding region. These peptides, fragments or other subunits of albumin which contain the binding region VI thus can also be modified in the manner of the invention as set forth herein so as to reduce or eliminate unwanted binding of trace metals such as nickel or copper in those applications wherein such reduction or elimination is desirable. Binding region VI in the human serum albumin is located at the n-terminal region and which includes residues 1–3 of the amino acid chain, and has the sequence Asp-Ala-His.

In accordance with one of the preferred embodiments of the present invention, a modification which can achieve the desired reduction of affinity is made by truncating the serum albumin at the n-terminal end by at least one amino acid so that the affinity to trace metals is reduced. In the particularly preferred embodiment, the truncation will comprise the removal of a single amino acid from the n-terminal end of the serum albumin which is sufficient to achieve reduction or elimination of trace metal binding, but will not have any other appreciable effects on the albumin and its normal properties. However, although a truncation of a single amino acid will be sufficient to accomplish the reduction in metal affinity, truncations of more than one amino acid from the n-terminal end will also accomplish the purpose of lowering the albumin's affinity to trace metals.

Similarly, other modifications which alter the n-terminal end of the albumin will also be suitable in reducing or eliminating the affinity to undesirable trace metals. For example, such mutations may take the form of elongation or insertion of suitable amino acids so as to change the character of the n-terminal region and make the binding site region VI far less likely to bind and/or retain trace metals. Any elongation or insertion at the n-terminal region or within binding region VI that is sufficient to either sterically hinder the binding site VI or eliminate vital binding interactions in this region will be suitable for use in the present invention and will provide the interference necessary to inhibit or eliminate the binding of the albumin with trace metals including nickel and copper. Although a variety of amino acid sequences of differing sizes will be useful in accordance with the invention, elongations or insertions of peptides having from about 1 to 10 amino acids are generally preferred.

In accordance with the present invention, it is preferred to obtain a serum albumin having a truncation or deletion especially at the three flexible residues on the n-terminus, namely the Asp-Ala-His residues which are connected to the sequence Lys-Ser-Glu at the n-terminal region. In a particularly preferred embodiment of the invention, the desired albumin sequence will have a single amino acid truncation which removes the Asp residue at the n-terminal end and which will thus have the sequence Ala-His-Lys-Ser-Glu. (SEQ ID NO:1) . . . This embodiment is particularly preferred because it is least likely to produce an antigenic response yet should significantly reduce trace metal binding at the n-terminal end. Similarly, deletions or truncations of a size greater than a single amino acid are also contemplated by the invention, and will also result in an improved albumin which is less likely to bind to metals such as copper and nickel. Accordingly, other n-terminal deletions in the region of the three flexible residues at the n-terminal end are also suitable in the invention, and thus n-terminal sequences such as His-Lys-Ser-Glu (SEQ ID NO:2) . . . and Lys-Ser-Glu . . . will also be useful in the modified albumin of the invention. Additionally, any other further truncation of the n-terminal end that is sufficient so as to either sterically hinder the binding site VI or eliminate vital binding interactions at that region will be suitable as a modified albumin in accordance with the invention.

In addition, other suitable forms of the present invention will include those additions or substitutions of the amino acid sequence at the n-terminal region or the binding site VI which are sufficient to disrupt the binding of trace metals such as copper and nickel to the albumin, either by providing sufficient steric hindrance to inhibit metal binding or by disrupting or eliminating vital binding interactions. For example, any suitable leader sequence or other elongation at the n-terminal sequence Asp-Ala-His-Lys-Ser-Glu (SEQ ID NO:3) . . . will be useful to provide a modified albumin in accordance with the invention.

Furthermore, in another preferred embodiment in accordance with the invention, any substitutions at the histidine residue at position 3 will also produce an improved non-metal binding modified albumin because the histidine is a critical aspect of the copper and nickel binding. The preferred substituted modified albumin sequence in accordance with the invention thus has the sequence Asp-Ala-X-Lys-Ser-Glu (SEQ ID NO:4) . . . , wherein X represents any amino acid substitution (or insertion or deletion) which will provide steric hindrance or disrupt vital binding interactions sufficient to reduce or eliminate the binding of metals such as copper and nickel to the serum albumin. Because of the critical nature of the histidine at position 3, any amino acid insertions in the leader sequence before this histidine will generally be sufficient to disrupt the metal binding.

Accordingly, in accordance with the invention, it is also preferred to provide a modified albumin with reduced affinity to trace metals by making a mutation in the serum albumin at the histidine located at position 3 of the amino acid chain, which as indicated above is part of the sequence X—X-histidine which appears to be a key site for binding of metals such as nickel and/or copper. It has been observed that at physiological pH, copper is bound with high affinity to this site ($K_a=1.6 \times 10^{16}$ $M^{-1}$), perhaps the highest reported binding constant for any bound ligand to serum albumin. By disruption of this binding site, either through replacement or deletion of the histidine residue, or through other elongations or insertions at or around that site which are sufficient to interfere with the structural integrity of the binding site, the resulting modified albumin will have reduced or eliminated binding affinity for trace metals.

In the preferred mode of producing the modified albumins of the present invention, said albumins are produced via recombinant methods wherein the nucleic acids coding for the albumin proteins are genetically engineered so as to manufacture an albumin with the desired modifications to its n-terminal region as set forth above. Accordingly, the present invention also contemplates the production, isolation and/or purification of nucleic acid sequences coding for the modified albumins of the present invention. However, numerous other methods which are conventionally employed to obtain modified proteins, such as physical, chemical or enzymatic methods, may also be suitable to produce the modified albumins of the invention as would be readily understood by one skilled in this art.

In accordance with the present invention, the modified serum albumins of the invention can thus be used in a variety of applications ranging from blood products and blood substitutes to cosmetics and other topical applications. In general, the modified albumins of the present invention, once prepared using any of the conventional methods set forth above which would be apparent to one of ordinary skill in this art, can be made into compositions that will be useful, e.g., as safe and effective blood products such as a blood volume expanders. As would also be recognized by one skilled in the art, the albumins of invention can be made into suitable blood replacement compositions in any of a variety of conventional methods well known in the art using physiologically acceptable fluids or other materials conventionally used in preparing other blood replacement products. Once prepared into physiologically compatible blood replacement solutions, the modified albumins of the present invention can be administered as needed to increase blood volume or, in the case of an albumin which has also been modified to transport oxygen, to enhance oxygen transport in the patient's circulatory system, for example, for patients who have suffered severe loss of blood, or during surgical operations. The modified albumins of the present invention may also be useable in a variety of other applications, such as those in the field of cosmetics or medical applications which currently employ albumin, either in the form of HSA or bovine serum albumin (BSA), or other similarly related compounds.

The modified albumins of the present invention may also be prepared into pharmaceutical compositions through introduction of the albumin in a physiologically acceptable vehicle, excipient or carrier. These pharmaceutical compositions would preferably be those compositions which would normally be prepared using non-modified albumin, and thus the preparation of these compositions in accordance with the present invention can be accomplished using conventional means already employed for such compositions, as would be understood by one skilled in this art.

In summary, the uses of the modified albumin of the present invention will be as expansive as those current uses of non-modified albumin and range from blood volume expanders, cosmetics, medicaments and pharmaceutical compositions as discussed above for possible use in shampoos, eye drop solutions, medicinal additives, and so on as would be recognized by one of ordinary skill in these arts. In addition, the large scale production of recombinant modified albumin will provide a safer and more tolerable albumin product and can potentially be employed in a variety of new applications including dairy products (e.g., nursing formulas, particularly for the many children that have been diagnosed as being allergic to bovine albumin of cows milk) and other dietary supplements (e.g., those where natural animal serum albumins would not be suitable). In all of these cases, the modified albumin of the invention with reduced affinity to trace metals will thus be far less likely to produce allergic reactions or other harmful conditions when compared to non-modified serum albumins which will have a significantly higher level of trace metals.

Finally, another important application contemplated by the present invention will be the utilization of the modified albumins of the invention in conjunction with the production of this protein through transgenic plants. The reason that the modified albumin of the invention will be particularly suitable to recombinant production in large quantities in transgenic plants is that such albumins will be very likely to pick up unwanted trace metals such as nickel or copper from the plants, and so the modification of the amino acids at the n-terminal region in accordance with the present invention will allow albumin to be produced in large quantities from transgenic plants without the potentially dangerous accumulation of metals that would otherwise occur.

It is thus submitted that the foregoing embodiments are only illustrative of the claimed invention, and alternative embodiments well known or obvious to one skilled in the art not specifically set forth above also fall within the scope of the claims.

In addition, the following examples are presented as illustrative of the claimed invention, and are not deemed to be limiting of the scope of the invention, as defined by the claims appended hereto, in any manner.

EXAMPLES

Example 1

Addition of the following amino acids to the n-terminus, Glu-Ala-Glu-Phe-Asp-Ala-His (SEQ ID NO:5), in the recombinant albumin identified as NCP control number A99-13,2393) resulted in greatly reduced coloration of the purified recombinant albumin. This albumin was prepared by conventional recombinant means normally used to obtain albumin from nucleic acids with the nucleic acids being recombined so as to have a sequence coding for the mutated albumin (either directly or through degenerate sequences). The reduction in coloration reflects the reduction in the bound trace metals and was quantitatively demonstrated by the reduction in $A_{400}$ for the albumin of the invention versus normal rHSA when produced and purified under otherwise identical conditions.

Figure 2:
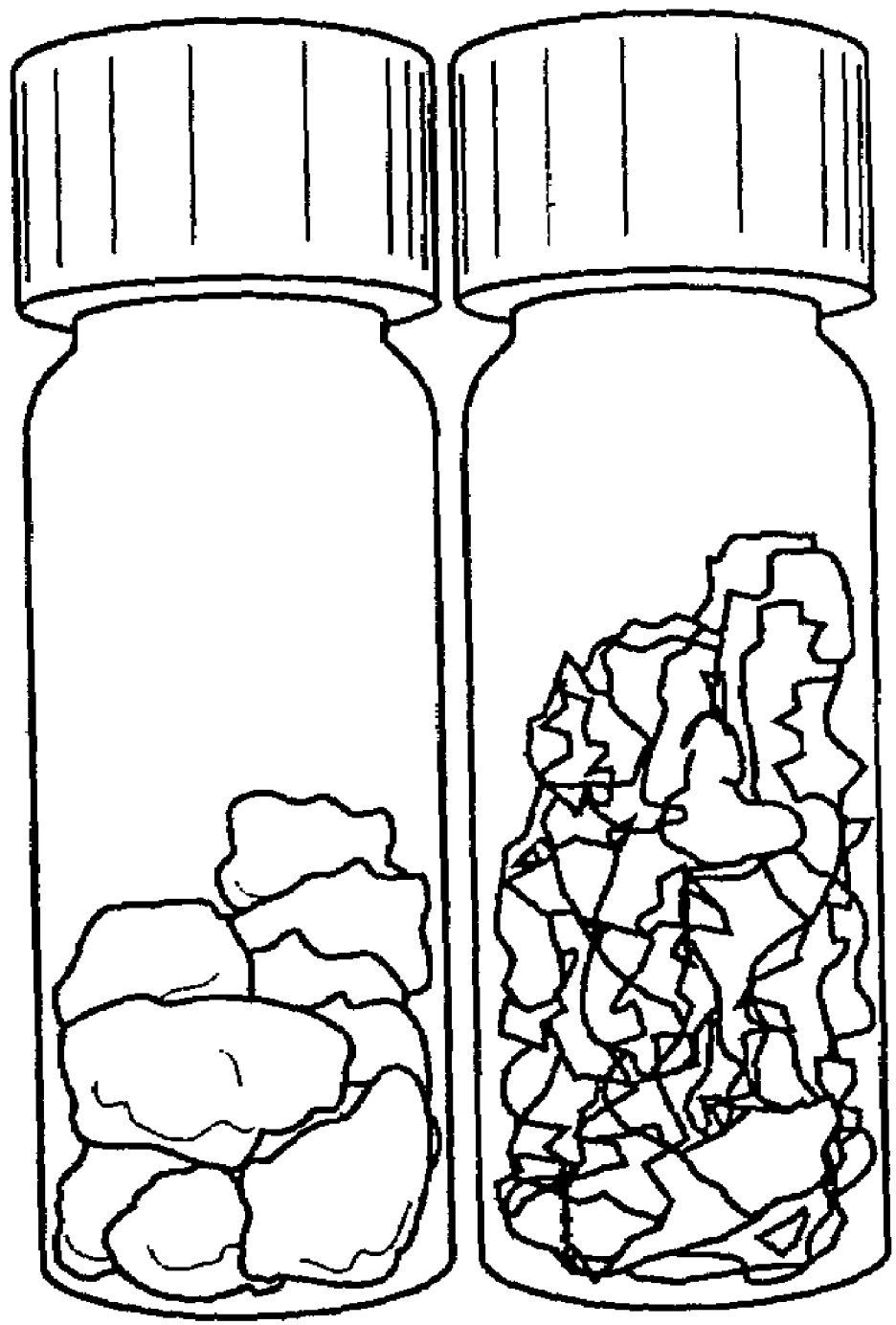
FIG. 2 is a photographic view of a serum albumin which has been mutated in accordance with the present invention (left side) and which is virtually free of trace metals as compared to a non-modified serum albumin (right side) which retains far greater trace metals such as nickel and copper than the modified albumin of the present invention.

The dramatic reduction in the binding of trace metals in this example is best observed in FIG. 2, which shows that the serum albumin which has been mutated in accordance with the present invention (left side) is virtually free of trace metals as compared to a non-modified serum albumin (right side) which retains far greater trace metals such as nickel and copper than the modified albumin of the present invention.

Accordingly, these tests confirmed that the modified serum albumin in accordance with the present invention had significantly reduced binding to trace metals when compared to the unmodified recombinant human serum albumin.

Example 2

A culture grade human serum albumin was prepared in accordance with the invention which included an extended amino acid terminus at the n-terminal region [provide sequence added]. This modified Culture grade recombinant albumin (A25799-099) with the extended amino acid terminus was then analyzed via metal analysis in comparison with a non-modified A11400-199×NCP "Ultrapure" (normal albumin sequence) preparation that was purer in albumin quality than the cruder Culture grade serum albumin which had been modified in accordance with the invention, but which had not been purified and had not been completely removed of salts. Despite the absence of the purification steps, as observed in the attached Table 1, the modified albumin in accordance with the invention was more than 16 times lower in Copper than the non-modified Ultrapure albumin. When salts and other non-bound metals are more thoroughly removed as would be the case in normal albumin preparations for use, this factor will increase by another 6 times, and the modified albumins of the invention will be more than 96 times lower in Copper (and/or other similar trace metals) than non-modified versions.

TABLE 1

| | rHSA A25799-099 | | | rHSA A11400-199x | | |
|---|---|---|---|---|---|---|
| | Metals, mg/kg (dry) | Limit of Detection | Analyzed on | Metals, mg/kg (dry) | Limit of Detection | Analyzed on |
| Aluminum | 24 | 9.93 | Jun. 21, 2000 | 7.17 | 1.99 | May 16, 2000 |
| Antimony | <14.9 | 14.9 | Jun. 21, 2000 | <2.99 | 2.99 | May 16, 2000 |
| Arsenic | <9.93 | 9.93 | Jun. 21, 2000 | <1.99 | 1.99 | May 16, 2000 |
| Barium | <2.98 | 2.98 | Jun. 21, 2000 | 3.11 | 0.60 | May 16, 2000 |
| Beryllium | <0.50 | 0.5 | Jun. 21, 2000 | <0.10 | 0.10 | May 16, 2000 |
| Boron | 16.1 | not deter. | Jun. 21, 2000 | <4.98 | 4.98 | May 16, 2000 |
| Cadmium | <1.49 | 1.49 | Jun. 21, 2000 | <0.30 | 0.30 | May 16, 2000 |
| Calcium | 63.8 | 3.48 | Jun. 21, 2000 | 61.1 | 0.70 | May 16, 2000 |
| Chromium | <4.97 | 4.97 | Jun. 21, 2000 | <1.00 | 1.00 | May 16, 2000 |
| Cobalt | <2.48 | 2.48 | Jun. 21, 2000 | 1.15 | 1.15 | May 16, 2000 |
| Copper | 19.7 | 0.99 | Jun. 21, 2000 | 322.3 | 0.20 | May 16, 2000 |
| Iron | <0.50 | 0.5 | Jun. 21, 2000 | 69.4 | 0.10 | May 16, 2000 |

TABLE 1-continued

| | rHSA A25799-099 | | | rHSA A11400-199x | | |
|---|---|---|---|---|---|---|
| | Metals, mg/kg (dry) | Limit of Detection | Analyzed on | Metals, mg/kg (dry) | Limit of Detection | Analyzed on |
| Lead | <9.93 | 9.93 | Jun. 21, 2000 | <1.99 | 1.99 | May 16, 2000 |
| Lithium | 0 | not deter. | Jun. 21, 2000 | <9.97 | 9.97 | May 16, 2000 |
| Magnesiu | 8130 | 4.97 | Jun. 21, 2000 | 1.79 | 1.00 | May 16, 2000 |
| Manganes | 5.17 | 1.24 | Jun. 21, 2000 | 0.55 | 0.25 | May 16, 2000 |
| Molybden | <9.93 | 9.93 | Jun. 21, 2000 | <1.99 | 1.99 | May 16, 2000 |
| Nickel | <2.98 | 2.98 | Jun. 21, 2000 | 7.09 | 0.60 | May 16, 2000 |
| Phosphor | 14500 | 14.9 | Jun. 21, 2000 | 2050 | 2.99 | May 16, 2000 |
| Potassium | 447 | 49.7 | Jun. 21, 2000 | 1180 | 9.97 | May 16, 2000 |
| Selenium | <19.9 | 19.9 | Jun. 21, 2000 | <3.99 | 3.99 | May 16, 2000 |
| Silicon | 99.6 | 4.97 | Jun. 21, 2000 | 74.5 | 1.00 | May 16, 2000 |
| Strontium | 0 | not deter. | Jun. 21, 2000 | <7.98 | 7.98 | May 16, 2000 |
| Thallium | <24.8 | 24.8 | Jun. 21, 2000 | <4.98 | 4.98 | May 16, 2000 |
| Tin | 3.48 | not deter. | Jun. 21, 2000 | <6.98 | 6.98 | May 16, 2000 |
| Titanium | 1.21 | 0.99 | Jun. 21, 2000 | <0.20 | 0.20 | May 16, 2000 |
| Vanadium | <0.99 | 0.99 | Jun. 21, 2000 | <0.20 | 0.20 | May 16, 2000 |
| Zinc | 8.15 | 1.99 | Jun. 21, 2000 | 4.82 | 0.40 | May 16, 2000 |
| Silver | <0.99 | 0.99 | Jun. 21, 2000 | 0.28 | 0.20 | May 16, 2000 |
| Sodium | 27100 | 4.97 | Jun. 21, 2000 | 4540 | 1.00 | May 16, 2000 |

Once again, these metal analyses showed that the modified serum albumin in accordance with the present invention had significantly reduced binding to trace metals such as Copper when compared to the unmodified human serum albumin.

What is claimed is:

1. A pharmaceutical or cosmetic composition comprising an isolated recombinant human serum albumin that can substitute for natural human serum albumin having at least a three-amino acid truncation at its N-terminal end that is sufficient to reduce the albumin's affinity to trace metals and a physiologically acceptable vehicle, carrier or excipient.

2. A pharmaceutical or cosmetic composition according to claim 1 wherein the isolated human serum albumin is produced using a transgenic plant.

3. An isolated non-natural human serum albumin having at least one mutation at its N-terminal end sufficient to cause steric hindrance at the binding region VI and thereby reduce the albumin's affinity to trace metals.

4. An isolated human serum albumin according to claim 3 wherein the mutation comprises an elongation or insertion.

5. A pharmaceutical or cosmetic composition comprising the serum albumin according to claim 3 and a physiologically acceptable vehicle, carrier or excipient.

6. A pharmaceutical or cosmetic composition comprising an isolated recombinant human serum albumin that can substitute for natural human serum albumin having at least a three-amino acid truncation at its N-terminal end, wherein the truncation is sufficient to sterically hinder the binding site VI so as to reduce the albumin's affinity to trace metals, and a physiologically acceptable vehicle, carrier or excipient.

* * * * *